United States Patent [19]
Leying et al.

[11] Patent Number: 6,136,531
[45] Date of Patent: *Oct. 24, 2000

[54] METHOD OF QUANTITATIVELY DETECTING NUCLEIC ACIDS

[75] Inventors: Hermann Leying, Bichl; Matthias Hinzpeter, München; Hans-Peter Fritton, Mörlenbach; Clemens Doppler, Brühl; Heiko Wittor, Tutzing, all of Germany

[73] Assignee: Roche Diagnostics GmbH, Mannheim, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/960,153

[22] Filed: Oct. 29, 1997

Related U.S. Application Data

[63] Continuation-in-part of application No. 08/646,958, May 8, 1996.

[30] Foreign Application Priority Data

May 8, 1995 [DE] Germany ............... 195 16 196

[51] Int. Cl.$^7$ .................................................. C12Q 1/68
[52] U.S. Cl. ..................... 435/6; 435/91.1; 435/91.2; 435/183; 536/22.1; 536/23
[58] Field of Search ................. 435/6, 91.2, 183; 536/22.1, 23

*Primary Examiner*—Kenneth R. Horlick
*Assistant Examiner*—Janell E. Taylor
*Attorney, Agent, or Firm*—Fulbright & Jaworski, LLP

[57] ABSTRACT

The invention describes a method of quantitatively detecting specific nucleotide sequences. Said method is essentially characterized in that a single-stranded nucleic acid, particularly mRNA, which has been isolated from a mixture, e.g. a biological sample, is hybridized in solution, with a polynucleotide sequence which is essentially complementary to the sequence to be determined; the nucleic acid is then immobilized on a solid phase, and the amount of bound hybrid is determined. It has proven to be particularly advantageous if the binding to the coated solid phase is accomplished with the aid of the specifically bindable chemical group which is coupled to the sequence to be determined or to the polynucleotide probe sequence via a linker.

10 Claims, 8 Drawing Sheets

○ β-Actin (filled=transfected)
□ CAT

METHOD OF QUANTITATIVELY DETECTING NUCLEIC ACIDS

This application is a continuation of application Ser. No. 08/646,958, filed May 8, 1996, now abandoned.

This is application claims priority of a German PCT application, application Ser. No. 195 16 196.3, filed May 5, 1995.

The invention describes a method of quantitatively detecting specific polynucleotide sequences. Said method is essentially characterized in that a single-stranded nucleic acid, particularly mRNA, which has been isolated from a mixture, e.g. a biological sample, is hybridized in solution, with a polynucleotide sequence which is essentially complementary to the sequence to be detected; the nucleic acid is then immobilized on a solid phase, and the amount of bound hybrid is determined. It has proven to be particularly advantageous if the binding to the coated solid phase is accomplished with the aid of the specifically bindable chemical group which is coupled to the sequence to be detected or to the polynucleotide probe sequence.

To date, there are known several methods of detecting nucleic acids. They are usually based on the principle of hybridization. In most cases, the sequence to be determined is first immobilized on the solid phase and then, a labeled nucleic acid probe is added. The method is, however, time-consuming and difficult to accomplish for those who are not familiar with this technology. This applies in particular since hybridization to a solid phase is a process with little efficiency.

Alternatively, nucleic acids can also be determined via in situ labeling of the probe nucleic acid and fixation to the solid phase which is accomplished via a sequence-specific nucleotide sequence probe. In another method, two sequence-specific probes are used to process the nucleic acid to be determined. Both in situ labeling and hybridization with two probes to the solid phase are often not reproducible, i.e. quantification is either difficult or only possible with great inaccuracy; in addition, the experimental procedure is complex and, hence, less suitable for routine work in clinical diagnostics.

These methods and variants are known as Northern blot method, nuclease protection assay, and quantitative RT-PCR; today, they are part of standard methodology for the quantification of nucleic acids (T. Maniatis, Molecular Cloning: A Laboratory Manual, 2nd ed. (1989); R. E. Farell, RNA Modologies: A Laboratory Guide for Isolation and Characterization, Academic Press; J. W. Larrick, Trends Biotechnol. 10, 146–152 (1992); E. S. Kawasaki, A Guide to Methods and Applications (eds. Innis, M.A. et al) Academic Press).

Another known method for the detection of nucleic acids, especially mRNA, is the microtiter plate method wherein the hybridization reaction is allowed to occur in solution. Hybridization is usually accomplished with the aid of a biotin-labeled cDNA probe. Subsequently, the nucleic acid hybrids are immobilized via biotin label and detected in a conventional ELISA test using an antibody which specifically binds DNA/RNA (C. O. Yehle et al., Mol. Cell. Probes 1, 177–193 (1987); F. Countlee et al, J. Biol. Chem. 256, 11601–11604 (1990); EP 0 336 454). Moreover, instead of an antibody, it is also possible to use a suitable detection probe (sandwich hybridization, EP 0 192 168).

A drawback of methods of this kind is that only DNA can be used as a capture probe; this is due to the fact that the detection is accomplished with the aid of DNA/RNA-specific antibodies. Moreover, the system exhibits little sensitivity when conventional chromogenic substrates are used. Moreover, when photo-reactive substances are used as labeling reagents for nucleic acid probes, experience has shown that the sensitivity is insufficient and the handling of corresponding determination methods leaves much to be desired (EP 0 237 833).

A recently published method, where the RNA is first hybridized with a capture probe that is already immobilized in a microtiter plate well and subsequently labeled with a fluorescent intercalating agent and then detected (T. Okamoto et al, Anal. Biochem. 221, 202–204 (1994) eliminates these drawbacks only partially. Depending on the length of the capture probe, this method leads to elevated background signals since not only the RNA which is actually to be detected but also the immobilized capture probe.

It was, hence, an object of the present invention to provide a method of detecting a specific polynucleotide sequence which eliminates the drawbacks described in prior art methods, i.e. it must be easy to perform and automate and allow the quantitative detection of nucleic acids.

This object is accomplished with the aid of a method for the determination of a specific polynucleotide sequence in a sample mixture which comprises the following steps: the nucleic acids, particularly those with a poly-dA sequence (mRNA) are isolated and, if required, converted into single-stranded nucleic acids.

Subsequently, the single-stranded nucleic acid to be determined is labeled with a chemical group, which, via a linker function, is either covalently bound to the nucleic acid molecule or associated therewith. Suitable chemical groups are those which either mediate the binding to the solid phase or those which can be directly or indirectly detected. Specifically binding ligands such as biotin or haptens, i.e. digoxigenin, have proven to be advantageous as immobilizable chemical groups.

The labeled nucleic acid is then hybridized with a polynucleotide probe which covers at least one single-stranded base sequence that is essentially complementary to the sequence to be determined; this hybridization is carried out in solution and under conditions that support hybridization between the sequence to be determined and the complementary probe sequence. The probe sequence is labeled with a second chemical group that can be distinguished from the first such chemical group. Principally, it is also possible to use immobilizable or detectable chemical groups as mentioned above; however, the first group must not be identical to the second group.

The twice-labeled nucleic acid hybrid is bound to the solid phase via the one labeling group while the amount of bound hybrid and, hence, the amount of nucleic acid isolated from a given volume are quantified via the other labeling group.

The method of the invention has proven to be particularly advantageous for the quantification of nucleic acids which contain poly-dA sequences, such as mRNA. For the purpose of hybridization, it is possible to use all types of samples, especially anti-sense RNA and peptide nucleic acids (PNA). This is of particular importance since hybridization between PNA and RNA molecules is more efficient than between pure RNA molecules which in turn hybridize in a more efficient manner than DNA and RNA molecules.

When incorporating a large number of labels into the RNA to be detected or the DNA used for the detection procedure, it is possible to increase the measuring signal and, hence, the chromogenic detection of specific mRNA which to date has only been possible in a limited manner when using the aforementioned methods.

Another advantage of the method of the invention is that the probe used for immobilization is not labeled. This significantly reduces the background signal.

Moreover, it also an advantage of the method of the invention that the hybridization reaction is not carried out on the solid phase, but in solution. Hybridization in solution is a more efficient and significantly faster process.

In addition to the already mentioned chemical groups for the label, determinable groups such as enzymatically active groups, e.g. peroxidase or bgalactosidase, fluorescent groups such as fluorescin or corresponding derivatives, different types of chromophors, or luminescent groups are also suitable. These chemical groups can be either chemically or enzymatically incorporated into the nucleic acid. However, radioisotopes, e.g. when incorporated in the presence of a terminal transferase and/or T4 RNA ligase and in the presence of a correspondingly labeled nucleotide or oligonucleotide, have also proven to be suitable also suitable are labelled antibodies specific for the labels.

Moreover, it is also possible to employ a method for incorporating non-radioactively labeled deoxynucleotides into nucleic acids such as RNA molecules which contain at their 3'-ends at least one deoxynucleotide which carries a non-radioactive labeling group. A corresponding method is described in European patent application, file reference 95 102 669.9.

It has proven to be particularly advantageous when the labeling of the nucleic acid and/or the polynucleotide is carried out with a corresponding hapten such as biotin or digoxigenin which is available in the form of a complex in a platinum-containing compound such as {Pt (ethylenediamin)(Me$_2$SO) (hapten-NH(CS)NHCH$_3$}. The labeling is carried out with the correspondingly active form of such platinum complexes. Platinum compounds of this kind have proven to be particularly suitable as linkers and are usually referred to as "Universal Linkage System" (ULS) (EP 0 539 466/WO 92/01699). Groups that are coupled to platinum complexes have proven to be particularly advantageous as detectable, i.e. second chemical groups.

Another preferred embodiment of the invention uses a peptide nucleic acid derivative with a base sequence that is essentially complementary to the sequence to be determined instead of a labeled complementary polynucleotide probe.

Principally, the solid phase can be made of several materials and shapes including microparticles, known as beads, pores or non-permeable membranes; or the solid phase can be the inner surfaces of reaction vessels such as test tubes or microtiter plates. In a preferred manner, the present invention is carried out on coated microtiter plates (e.g. manufactured by Nunclon), especially those where streptavidin (SA) or avidin were used for the coating. Corresponding measures and/or solid phases are known to the expert and described in EP 0 344 578, for example.

The following is a description of the individual steps of the procedure in accordance with the invention in greater detail:

Approximately 10–20 μg of mRNA were isolated with suitable beads corresponding to information included in the mRNA isolation kit by Boehringer Mannheim. Quantification was carried out at OD$_{260/280\ nm}$, wherein 2 μg of mRNA in 500 μl of aqueous solution correspond to 0.1 OD$_{260\ nm}$.

Approximately 0.4 μg of biotin ULS were added to accomplish the labeling of approximately 10 μg of mRNA; the mixture was incubated for approximately 60 min at 65° C. and subsequently precipitated with ethanol and quantified over OD$_{260/280\ nm}$.

For the hybridization procedure, approximately 100–150 μl/well were prepared in a suitable hybridization buffer and heated up to approximately 50° C. A DIG-labeled DNA probe which was denatured was added to the reaction mixture after approximately 50 to 1000 ng/well of the biotin-labeled mRNA had been added by pipetting. An aqueous solution containing approximately 50% formamide, 0.1% lauryl sarcosin and 0.02% SDS (sodium dodecyl sulfate) has proven to be a particularly advantageous hybridization buffer. The hybridization procedure lasted between 30 min and 4 h at approximately 50° C. and 400 rpm; the hybridization time depends upon the length of the specific probe sequence and the stringency of the hybridization conditions, for example. Surprisingly, these hybridization conditions have proven to be particularly well suited for the specific detection of RNA. This fact is surprising as it ensures, on the one side, the necessary stringency, but also a rapid denaturing of proteins, e.g. as one would have expected in a protein-like coating.

Prior to preparing the hybridization mixture, portions of approximately 100 μl were pipetted into streptavidin-coated microtiter plate wells which were preheated to 50° C. Incubation was carried out at 50° C./400 rpm in approximately 5 min.

Subsequently, the solution was decanted and the remainder was washed 3 to 6 times at room temperature. The subsequent incubation with, for example, POD-labeled <DIG> antibody was carried out over a period of 30 min at 37° C. and 400 rpm. Detection was accomplished, for example, by adding luminol/iodophenol and measuring after approximately 3 min.

Figure 1:
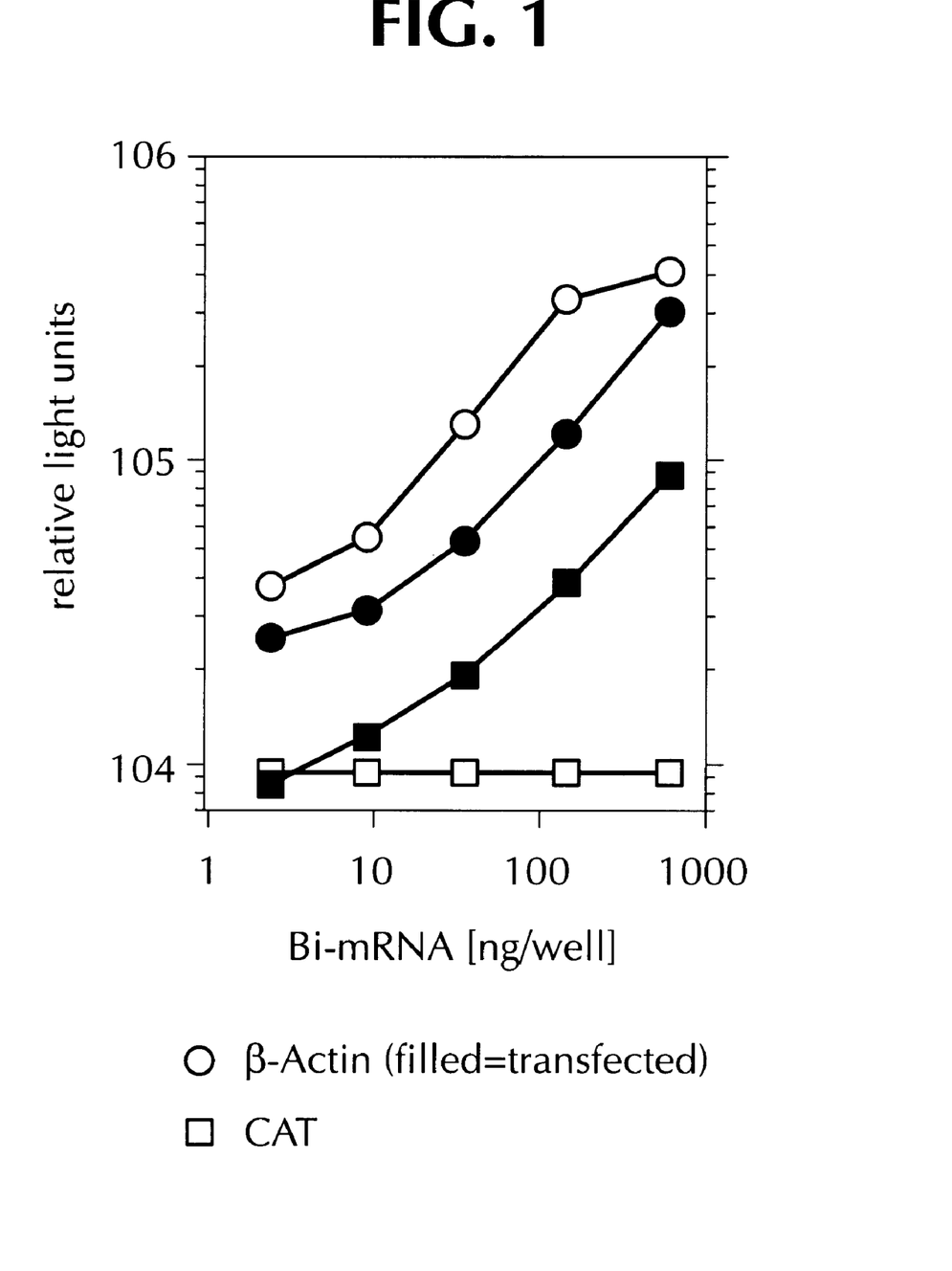
FIG. 1: Shows the result of examples 1–4, wherein ○=β-actin, a gene which is permanently present in cells; and □=CAT, a gene which is not present in eukaryotic cells; filled-out symbols mean "transfected".
Figure 2:
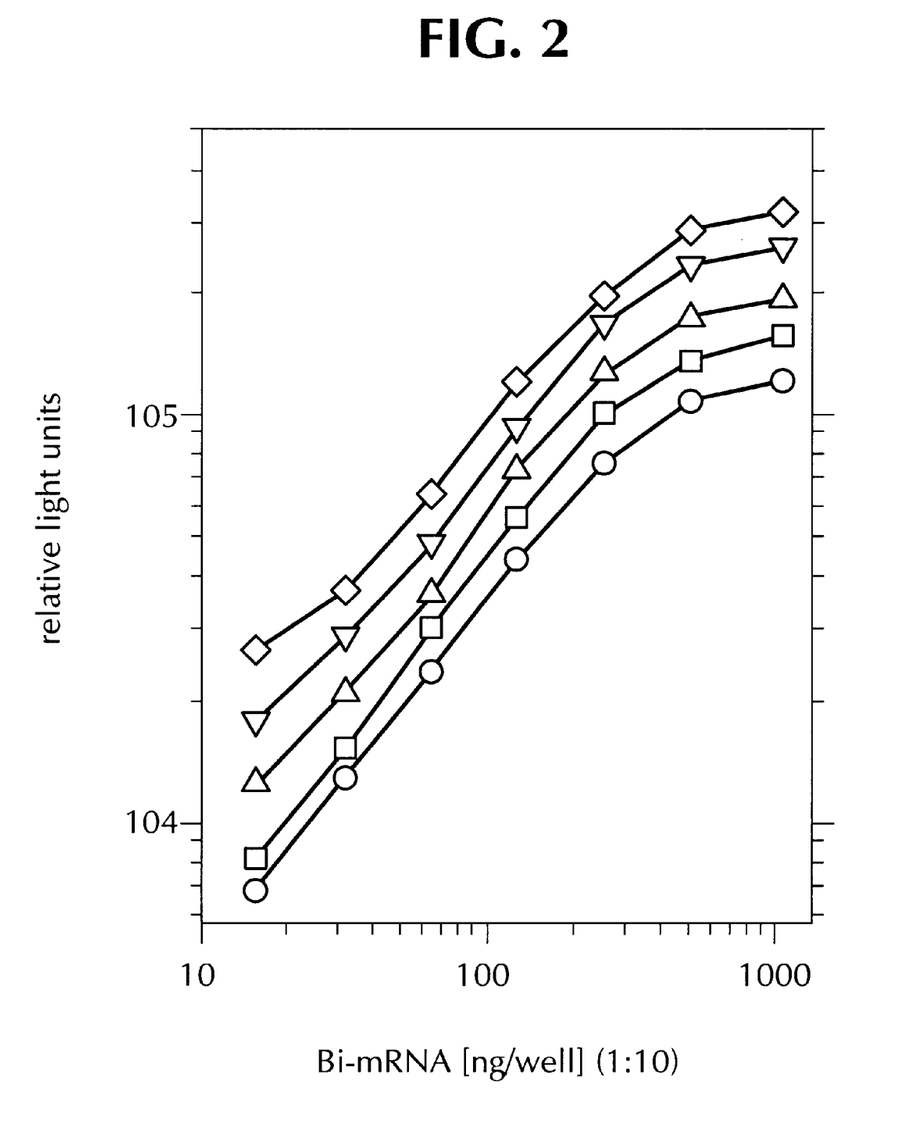
FIG. 2: Shows the influence of the amplicon concentration, wherein ○=0.5 μl, □=1 μl, Δ=2 μl, ∇=5 μl and ◊=10 μl of PCR fragment per well.
Figure 3:
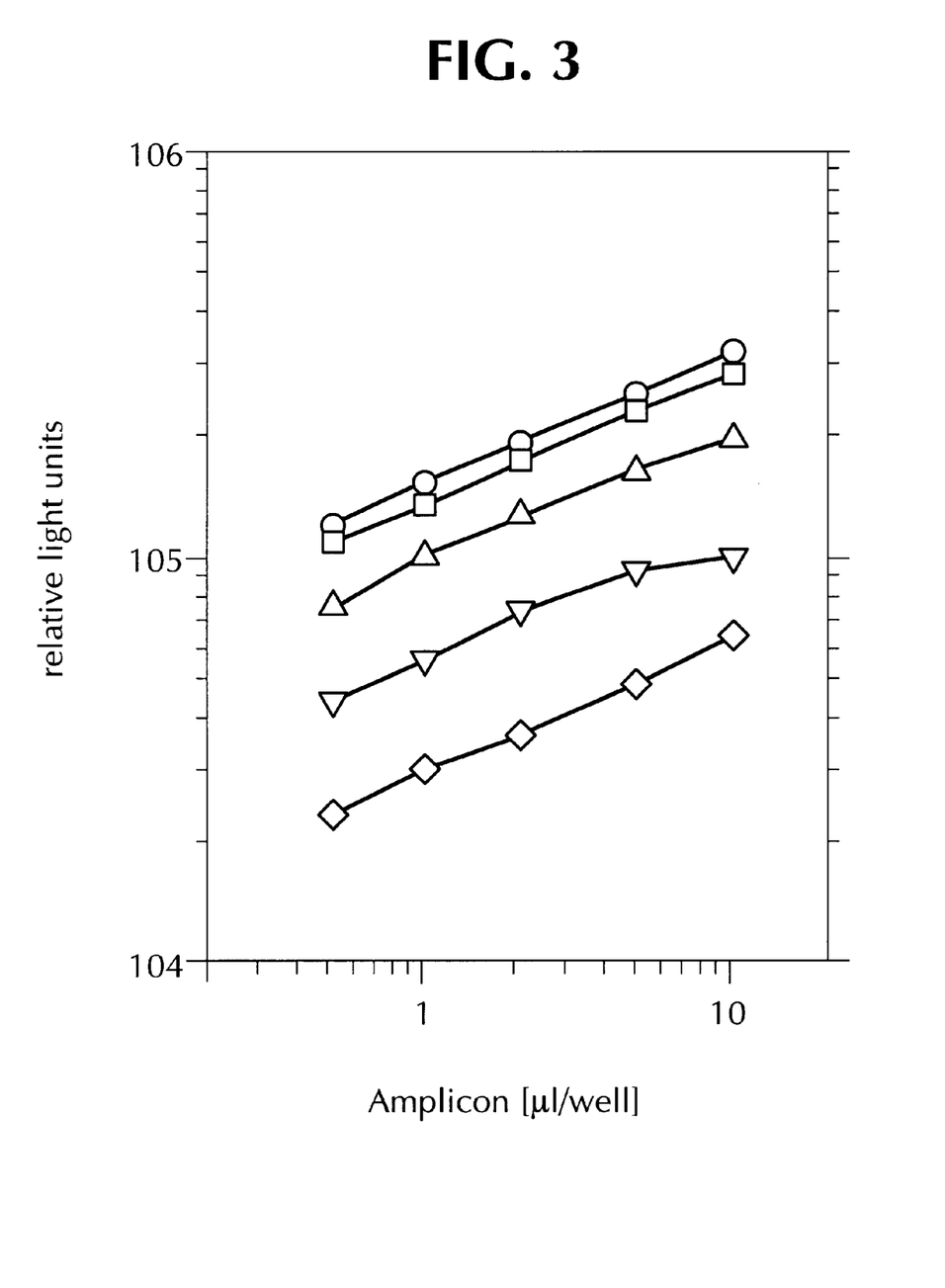
FIG. 3: Shows the influence of the amplicon concentration at a constant RNA concentration (○=1000 ng, □=500 ng, Δ=250 ng, ∇=125 ng and ◊=62 ng biotin (Bi)-mRNA/well).
Figure 4:
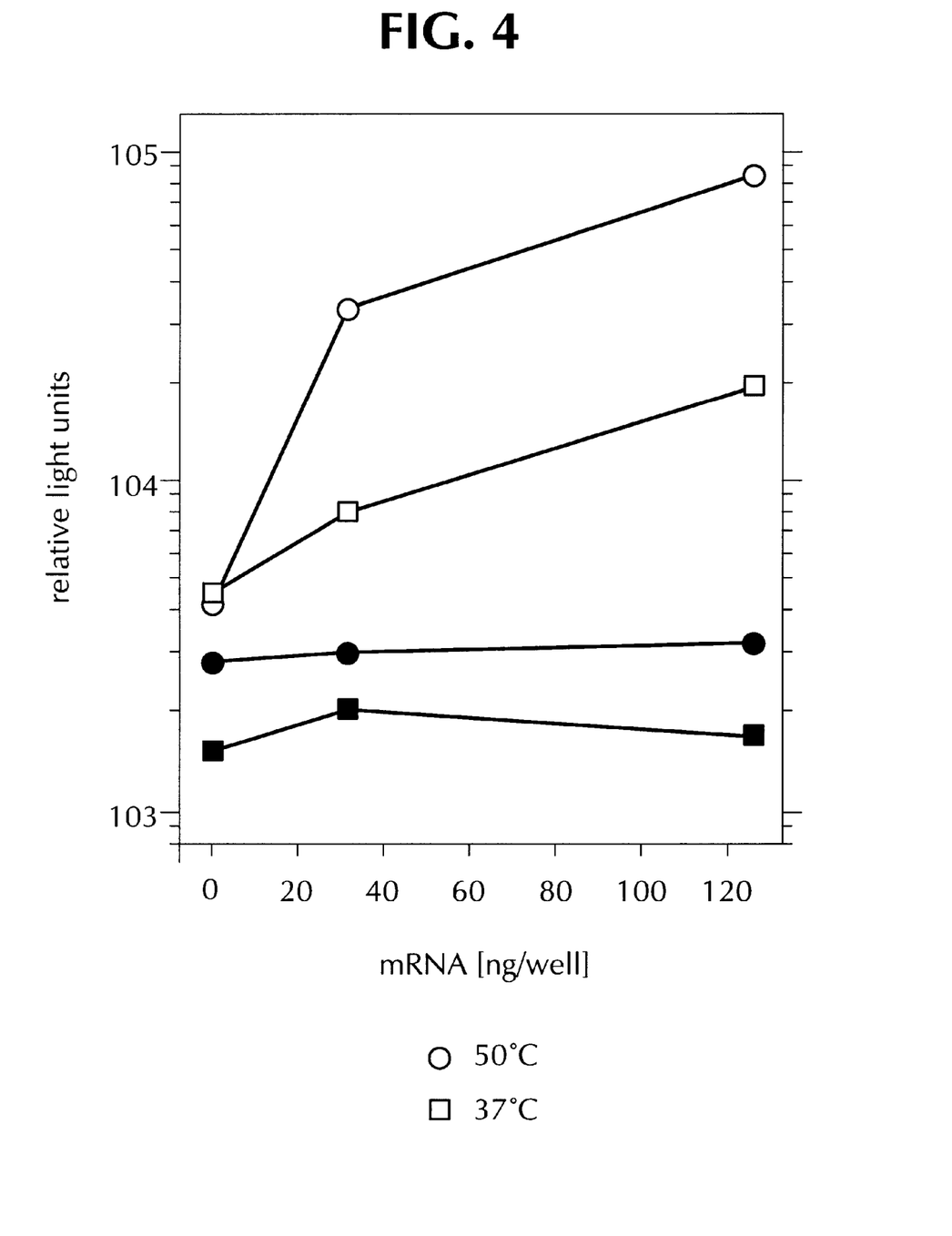
FIG. 4: Shows the influence of the hybridization temperature, ○=50° C. and □=37° C.
Figure 5:
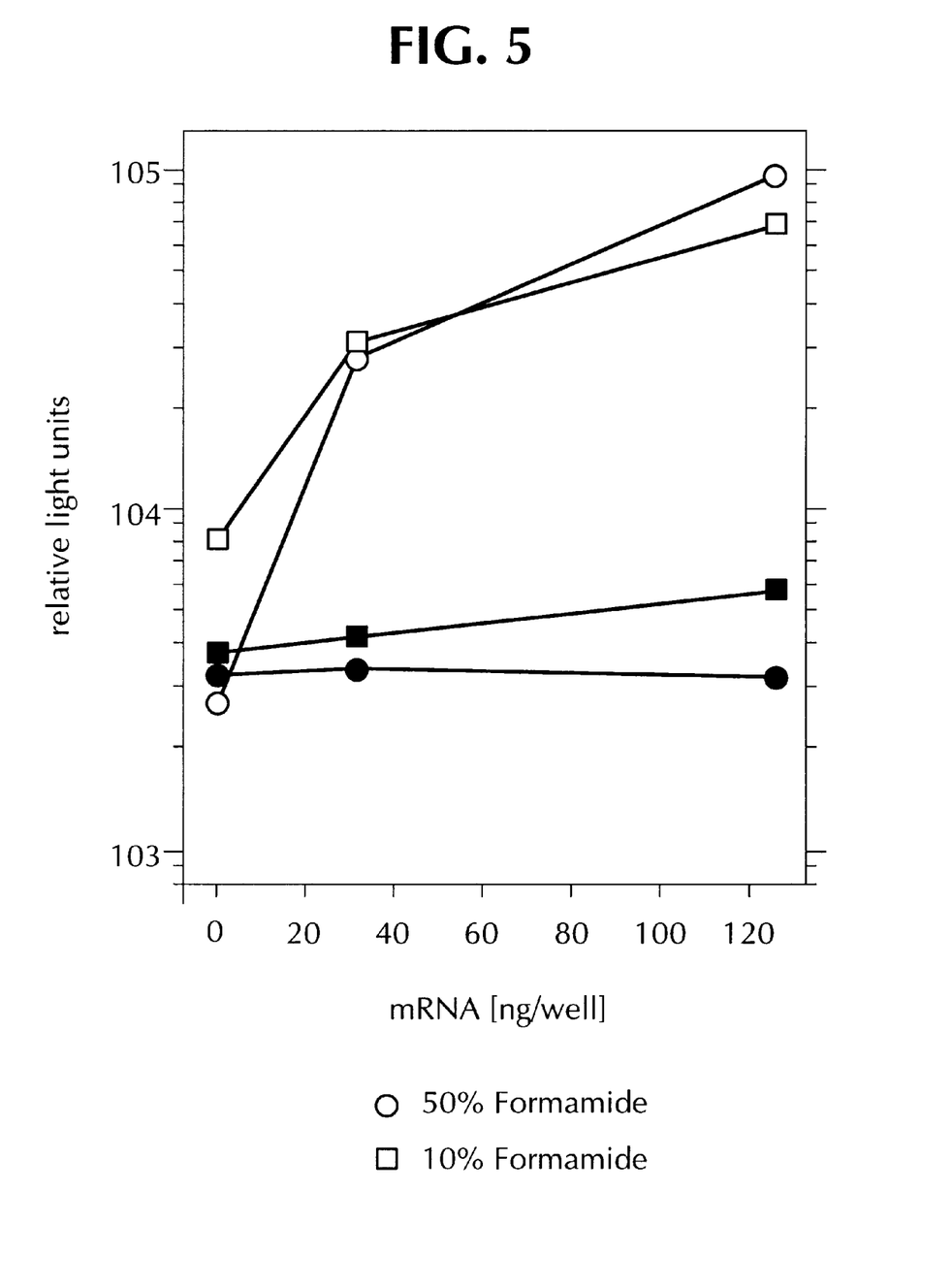
FIG. 5: Shows the influence of the formamide concentration, ○=50% formamide and □=10% formamide.
Figure 6A:
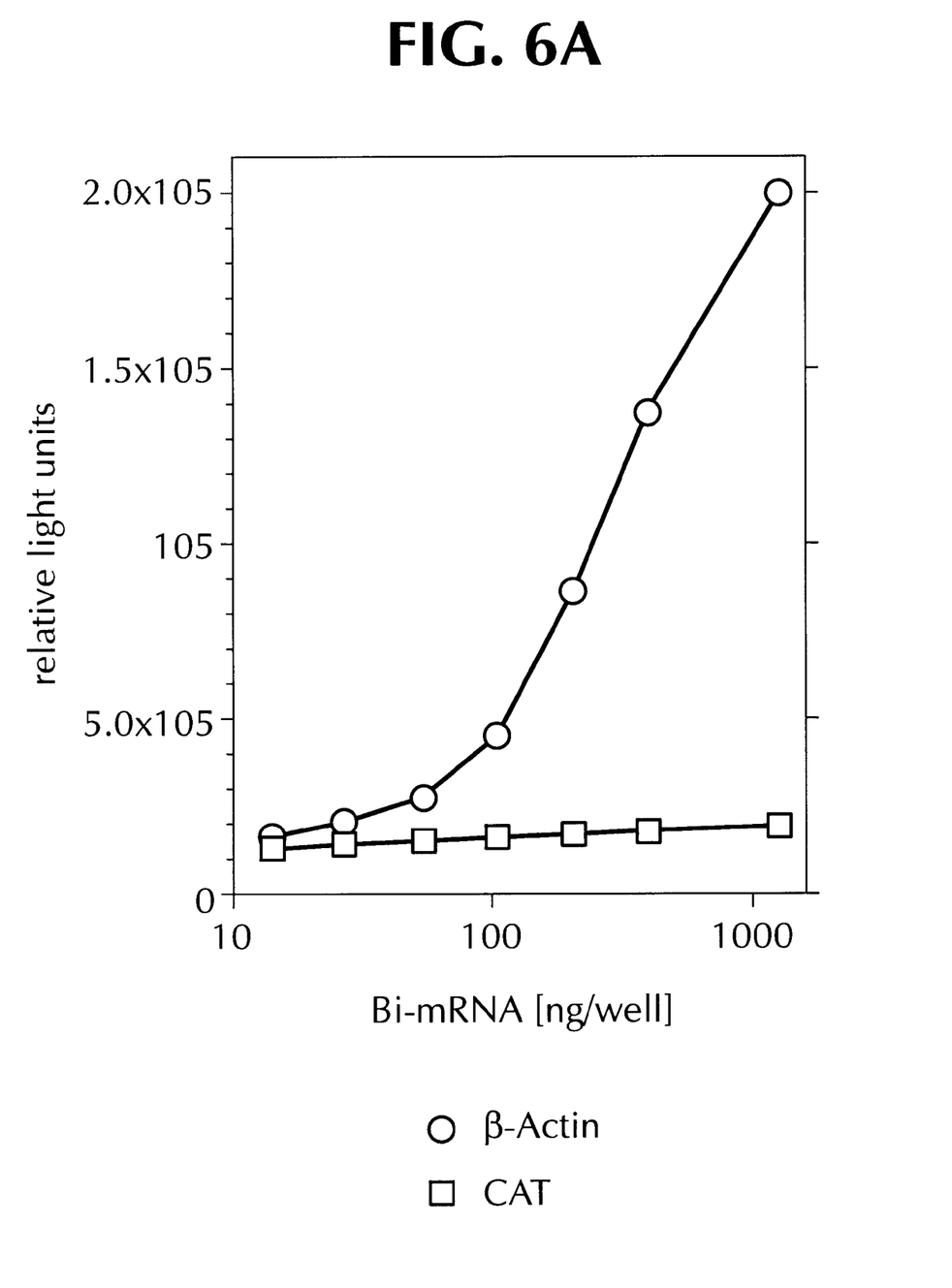
FIG. 6: Shows a comparison between the Northern ELISA procedure in accordance with the invention and the Northern blot assay according to prior art; mRNA is labeled with 1×562 25:1 Bio-ULS, and hybridization is accomplished with DIG-β-actin PCR fragment (838 bp) and/or CAT fragment; ○=β-actin, □=CAT.
Figure 6B:
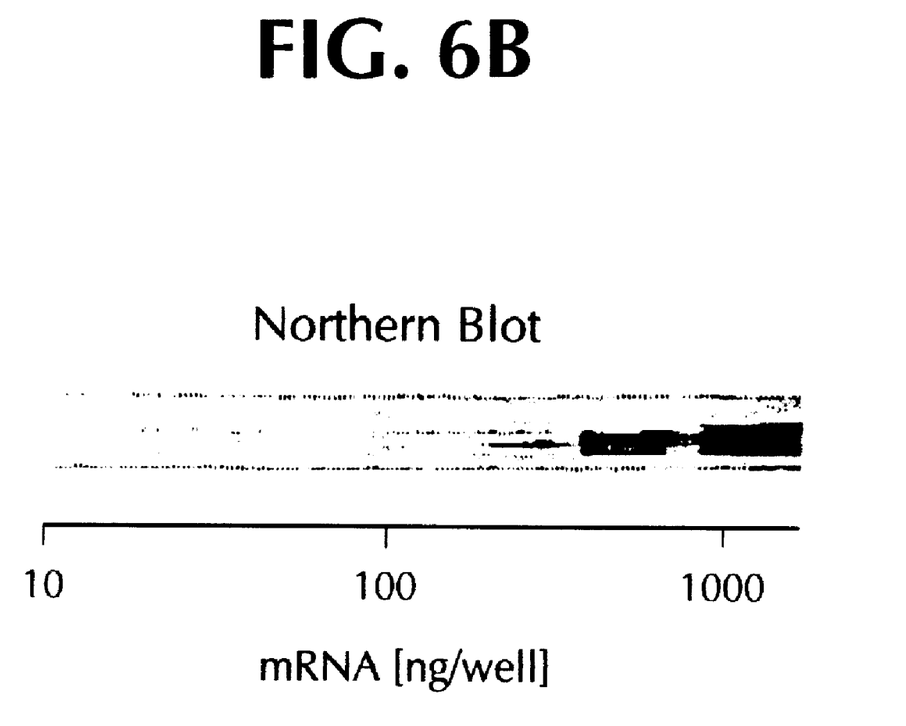
Figure 7:
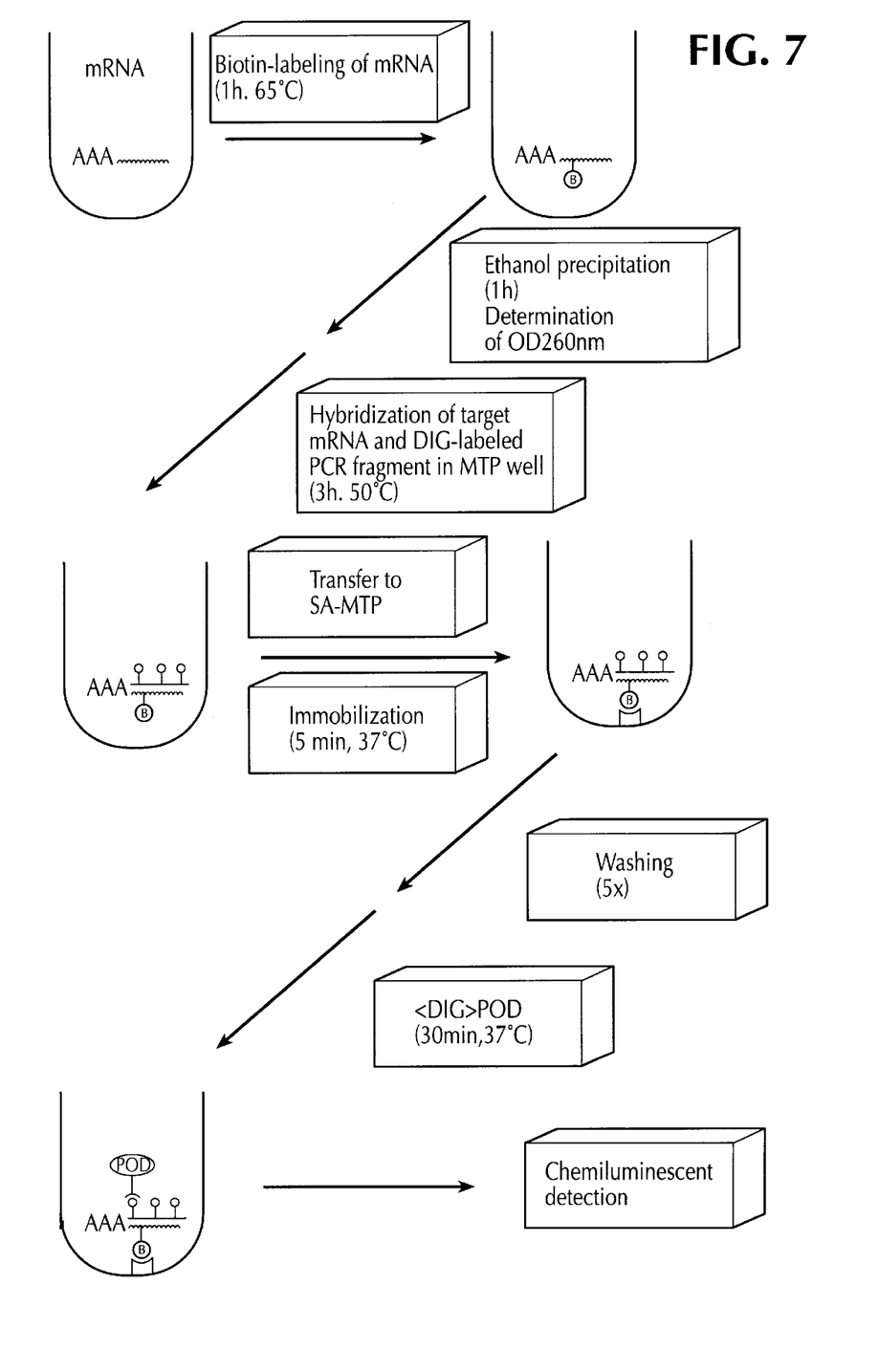
FIG. 7: Shows a reaction scheme of the method in accordance with the invention (Northern ELISA).

The following examples explain the invention in greater detail:

Total mRNA is labeled with biotin via a biotin platinum complex (Bio-ULS®). Subsequently, the mixture is hybridized with a transcript-specific, digoxigen (DIG) labelled DNA/RNA sample. After binding the mRNAs in a streptavidin (SA)-coated microtiter plate MTP, the specific RNA is detected with the aid of <DIG>POD.

This report describes the measurement of chloramphenicol acetyltransferase (CAT)-specific mRNA from cells that were transfected with CAT plasmid.

Materials and Methods

The pSV2CAT plasmid was obtained from Dr. Kösters (University Hospital Zurich, Switzerland). The DIP-STICK® elements for the quantification of the mRNA were obtained from Invitrogen (USA). Bio-ULS® was obtained from Kreatech (Netherlands). Boehringer Mannheim provided reagents such as Northern hybridization buffer (50% formamide, 5×SSC, 12% blocking reagents in maleic acid buffer, 0.1% lauryl sarcosin, 0.02% SDS), mRNA isolation kit, cell-culturing media and transfection reagent, reagents for the preparation of DNA probes, streptavidin-coated MTP, <DIG>POD, RNase-free conjugate dilution buffer (40 mM $KPO_4$, 1 mM EDTA, 0.25% BSA, pH 6.8) luminol/iodophenol as a chemiluminescent substrate and other additional reagents. The chemiluminescent measurements were carried out with the Microplate Luminometer LP 96P manufactured by Berthold.

EXAMPLE 1

Preparation of the DIG-labeled Probes

Methods for preparing suitable probes include amplification via PCR, random-primed labeling, and in vitro transcription. The probes used here were amplified in a PCR with the aid of suitable primers which are located within the coding sequence of the target RNA. Probe length for the actin probe: 838 bp; for the CAT probe: 367 bp (molar ratio in the PCR mix: dUTP/DIG-dUTP=3/1). The amplicon concentration was estimated via ethidium bromide staining and adjusted to approximately 20 ng/µl with triethanolamine (TE) pH 8.0.

EXAMPLE 2

Transfection Mixture

Hela cells were transfected with pSV2CAT using [1-(2, 3-dioleoyloxy)propyl]-$N_1N_1N$-trime according to the information given in the pack insert. The mRNA was isolated from the transfected cells and the untreated controls with the aid of magnetic beads.

Five culturing bottles each containing $5 \times 10^6$ cells (50 ml KM) were transfected with a total of 400 µg of plasmid over a period of 6 h: 24 h after transfection, the cells were treated with trypsin, removed, washed with PBS and the pellet was stored in liquid nitrogen ($4.4 \times 10^6$ living cells, 80% dead cells). The non-transfected controls were treated accordingly ($1.3 \times 10^7$ living cells, 5% dead cells).

EXAMPLE 3

Isolating mRNA and Labeling with Biotin

Following the information given in the pack insert, the mRNA was purified the aid of magnetic beads and the concentration was determined with the aid of DNA DIP-STICK®: Hela (+CAT):

10 µl with c=360 ng/µl, Hela (−CAT): 23 µl with c=500 ng/µl. Then labeling carried out for 1 h at 65° C. using biotin-ULS at a ratio of RNA/Bio-ULS=20/1 (W/W). The mixture was purified via ethanol precipitation and resused in water. The subsequent determination of the concentration with the aid of DNA DIPSTICK® gave the following result: Hela (+CAT): 9 µl with 200 ng/µl, Hela (−CAT): 29 µl with 80 ng/µl.

EXAMPLE 4

Northern ELISA Procedure

Portions of 120 µl of Northern hybridization buffer were added to the round bottom plate of a cell culture and heated up to 50° C. The DIG-labeled probes of example 1 were denatured for 5 min at 100° C. and then cooled in an ice-bath. Portions of 600/150/37.5/9.375 ng of Bi-mRNA were added to the hybridization buffer (dilution in TE). Subsequently, portions of 4 µl of DIG-labeled DNA probe were added. After 3 h of hybridization at 50° C. and 400 rpm, portions of 100 µl were pipetted onto a tBSA-SA plate that was pre-heated to 50° C.; the RNA obtained according to example 3 was bound for 5 min at 400 rpm. Subsequently, the mixture was decanted and washed 5 times with 0.1% SSC. Then portions of 100 µl of <DIG>POD conjugate (which is a conjugate of DIG specific antibody and peroxidase) (25 mU/ml) were added by pipetting and incubated for 30 min at 400 rpm and 37° C. Subsequently, the mixture was decanted and washed three times with 0.1% SSC. Then portions of 150 µl luminol/iodophenol were added and measured after 3 min.

TABLE 1

| Bi-mRNA | Non-transfected cells | | Transfected cells | |
| --- | --- | --- | --- | --- |
| [ng/well] | Actin | CAT | Actin | CAT |
| 600.0000 | 411368.0000 | 9254.0000 | 301705.0000 | 86979.0000 |
| 150.0000 | 332754.0000 | 8991.0000 | 120236.0000 | 39765.0000 |
| 37.5000 | 128350.0000 | 9052.0000 | 54657.0000 | 19252.0000 |
| 9.37502 | 56151.0000 | 9001.0000 | 32221.0000 | 12011.0000 |
| 2.3440 | 38877.0000 | 8757.0000 | 26047.0000 | 8331.0000 |

What is claimed is:

1. A method of quantitatively detecting a specific nucleic acid molecule in a sample comprising:
    a) labeling single-stranded nucleic acid molecules isolated from a sample with a first chemical group bound via a linker;
    b) hybridizing the labeled nucleic acid molecules in solution with a polynucleotide probe which includes at least one single-stranded base sequence that is essentially complementary to the nucleic acid molecule to be determined and at least one additional chemical group that differs from the first group, where said at least one additional chemical group, is a specifically bindable ligand or a enzymatically active group under conditions which support hybridization between the nucleic acid molecule to be determined and the complementary probe sequence so as to obtain a hybrid molecule;
    c) immobilizing the hybrid molecule on a solid phase via the first chemical group; and
    d) quantitatively measuring a level of the at least one additional chemical group on said solid phase as a quantitative measure of the specific nucleic acid molecule in said sample, by measuring enzymatic activity of said enzymatically active group or contacting said specifically bindable ligand with an antibody which binds to said specifically bindable ligand, and measuring binding of said antibody to said ligand.

2. The method of claim 1 wherein the isolated nucleic acid is mRNA, and the polynucleotide probe is an oligodeoxyribonucleotide, DNA, an oligoribonucleotide or RNA.

3. The method of claim 1 wherein the first chemical group bound via a linker is biotin or a biotin derivative.

4. The method of claim 1, wherein the additional chemical group is selected from the group consisting of a peroxidase, β-galactosidase, and a digoxigenin.

5. The method of claim 1 wherein the labeling is carried out with the aid of an activated platinum complex.

6. The method of claim 1 wherein the first or additional chemical group is incorporated in the nucleic acids either chemically or enzymatically.

7. The method of claim 6 wherein the enzymatic labeling is carried out with a terminal transferase or a T4 RNA ligase and a nucleotide or oligonucleotide labeled with a chemical group.

8. The method of claim 1 wherein the complementary polynucleotide probe is a peptide nucleic acid derivative.

9. The method of claim 1 wherein the solid phase is a coated solid phase.

10. The method of claim 9, wherein the solid phase is coated with a substance selected from the group consisting of avidin, streptavidin and a corresponding derivative thereof, and hybridization is carried out under conditions which support hybridization at approximately 50° C.

* * * * *

UNITED STATES PATENT AND TRADEMARK OFFICE
CERTIFICATE OF CORRECTION

PATENT NO. : 6,136,531
DATED : October 24, 2000
INVENTOR(S) : Leying et al It is certified that error appears in the above-identified patent and that said Letters Patent is hereby corrected as shown below:

In column 5, line 35-36, after "trime" insert -- thylammonium methyl sulfate, or "DOTAP" --.
In column 5, line 58, change "resused" to -- resuspended --.
In column 6, line 43, claim 1, delete -- or a enzymatically active group --.
In column 6, line 52-53, claim 1, delete -- by measuring enzymatic active of said enzymatically active group --.

Signed and Sealed this

Eighth Day of May, 2001

Attest:

NICHOLAS P. GODICI

Attesting Officer

Acting Director of the United States Patent and Trademark Office